United States Patent [19]

Ennis

[11] Patent Number: 4,464,174
[45] Date of Patent: Aug. 7, 1984

[54] TWO COMPARTMENT MIXING SYRINGE SEAL

[75] Inventor: James Ennis, Preston, Conn.
[73] Assignee: Silver Industries, Inc., Norwich, Conn.
[21] Appl. No.: 424,432
[22] Filed: Sep. 27, 1982
[51] Int. Cl.³ .............................................. A61M 5/00
[52] U.S. Cl. ..................................... 604/90; 604/236
[58] Field of Search ...................... 604/87, 88, 89, 90, 604/236, 237, 238, 200; 222/129, 145, 213, 386-389, 470, 490, 491

[56] References Cited

U.S. PATENT DOCUMENTS

| | | | |
|---|---|---|---|
| 2,869,544 | 1/1959 | Ratcliff et al. | 604/89 |
| 2,893,390 | 7/1959 | Lockhart | 604/238 |
| 3,076,456 | 2/1963 | Hunt, Sr. | 604/89 |
| 3,659,749 | 5/1972 | Schwartz | 604/90 |
| 4,233,975 | 11/1980 | Yerman | 604/236 |

*Primary Examiner*—John D. Yasko
*Attorney, Agent, or Firm*—Murray, Whisenhunt and Ferguson

[57] ABSTRACT

In a seal for two compartment mixing syringe having an outer barrel with an inner barrel partially disposed therein, and a seal on the dispensing end of the inner barrel, and a plunger disposed in the inner barrel, the improvement is wherein the seal is a combination of an aperture in the dispensing end of the inner barrel and a plug disposed in the aperture. The plug has a cylindrical portion of resilient and compressible material adapted to be compressibly disposed in the aperture but displaceable from the aperture by fluid pressure exerted by movement of the plunger in the inner barrel. A reduced diameter portion of the plug provides a fluid pathway between the inner barrel and the outer barrel when the cylindrical portion is displaced from the aperture by such fluid pressure. An increased diameter portion prevents the plug from passing through the aperture and into the outer barrel.

12 Claims, 5 Drawing Figures

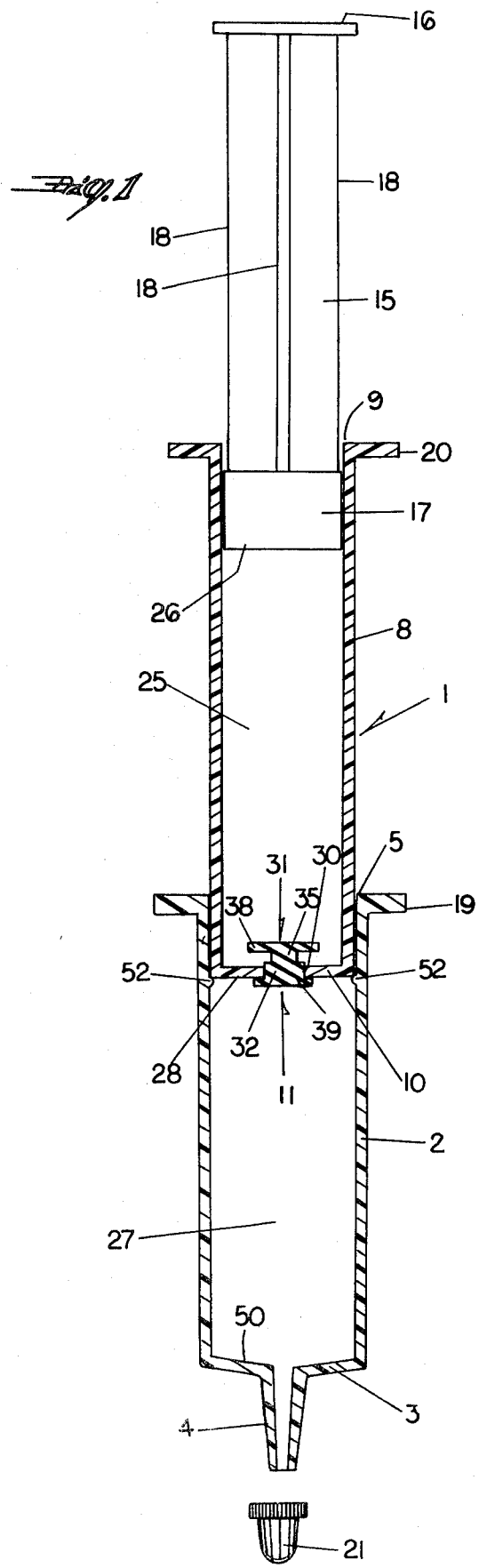
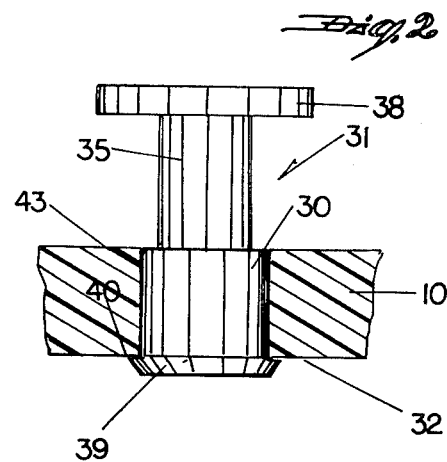
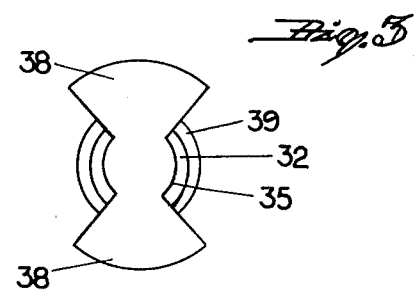
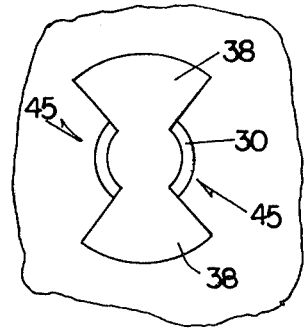
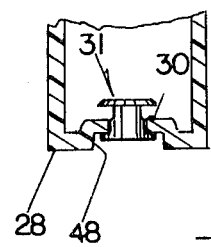

TWO COMPARTMENT MIXING SYRINGE SEAL

The present invention relates to a seal for a two compartment mixing syringe, and more particularly to such a seal which is less expensive to manufacture than prior art seals, is more reliable than prior art seals and improves mixing when the materials stored in the two compartments are mixed.

BACKGROUND OF THE INVENTION

Two compartment mixing syringes are well known to the art. These syringes consist of an outer barrel with a cannula end and an inner barrel disposed through an opened opposite end and partially into the outer barrel. A plugger is partially disposed within the inner barrel. A seal is provided at the dispensing end of the inner barrel and the seal is adapted to be displaced by pressure exerted on a fluid in the inner barrel, so that the fluid in the inner barrel can be flowed through the seal and into the outer barrel for mixing with a material contained in the outer barrel. After mixing has been completed, the inner barrel is moved into the outer barrel which causes the mixture to pass through the cannula and out of the syringe. The cannula is adapted for dispensing the mixture or adapted to hold a needle for injection of the mixture into a desired host, such as a animal.

Two compartment syringes of this nature are particularly applicable to mixtures which have a finite shelf life, but where separated ingredients of the mixture have much longer shelf lives. Thus, typically the separated ingredients are stored in the separate compartments of the syringe and are mixed shortly before the mixture is used. Typical examples thereof are powdered pharmaceuticals or other medicants stored in one compartment with a diluent or solvent therefor stored in another compartment. The diluent is then mixed with the pharmaceutical or medicant just prior to use.

A first compartment is formed between the outer barrel and the inner barrel and a second compartment is formed between the inner barrel and the plunger. Quite typically, the second compartment will contain a fluid, e.g. a liquid, and pressure applied to that fluid by way of digitally moving the plunger into the inner barrel displaces the seal from the dispensing end of the inner barrel and allows the fluid to flow into the first compartment (formed between the outer barrel and inner barrel) for mixing with the ingredients contained in the first compartment. After that mixing has been achieved, then the inner barrel is digitally moved into the outer barrel for forcing the mixture out of the cannula end of the outer barrel. As can therefore be appreciated, the seal on the dispensing end of the inner barrel is a most critical element of such two compartment mixing syringes. For example, if the seal should leak during storage, then unwanted prior mixing can occur and such prior mixing may destroy the usefulness of the resulting mixture. Further, since the seal must be displaced by digital pressure applied to the plunger, the seal must be fluid tight in the normal condition, but accurately displaceable by digital pressure on the plunger.

Typical two compartment syringes are shown in U.S. Pat. No. 3,052,239 and U.S. Pat. No. 3,380,451. However, a particularly advantageous seal is shown in the U.S. Pat. No. 3,685,514, the disclosure of which is incorporated herein by reference, particularly in regard to the general arrangement and operation of two compartment syringes. That patent discloses a cap of resilient and flexible material fitted over the dispensing end of the inner barrel. The cap is biased such that in storage the cap fits tightly over an aperture in the dispensing end of the inner barrel, but when pressure is applied to the fluid in the inner barrel that bias is overcome and the cap is displaceable from the aperture, thus, permitting the fluid in the inner barrel to pass into the outer barrel.

While the arrangement of that seal provides an exceptionally good fluid tight seal such that there is essentially no leakage of the fluid from the inner barrel to the outer barrel during storage, it does suffer from the disadvantage that the cap must be accurately produced and assembled in order to provide the biasing required for operation of the seal. This results in a more expensive seal. In addition, when pressure is applied to the fluid in the inner barrel, the biasing is gradually overcome and the seal gradually opens. In turn, there is a gradual dispensing of the fluid from the inner barrel into the outer barrel. While this gradual dispensing of the fluid is quite satisfactory for many applications, in other applications it is desired for that passage of fluid to be of a character to improve mixing, particularly where the fluid in the inner barrel and the material in the outer barrel are not quickly mixed and/or dissolved. Finally, this type of seal is subject to inadvertent mixing of the ingredients.

Accordingly, it would be of considerable advantage to the art to provide a seal for a two compartment mixing syringe wherein the seal may be very inexpensively manufactured, is most easy to assemble, and which will provide improved mixing of the fluid in the inner barrel with the material contained in the outer barrel, as well as avoid inadvertent mixing.

OBJECTS OF THE INVENTION

It is therefore an object of the invention to provide an improved seal for a two compartment mixing syringe wherein the seal is most inexpensive to manufacture and assemble onto the dispensing end of the inner barrel of the syringe. It is another object of the invention to provide such a seal where inadvertent pressure on the plunger will not normally be sufficient to displace the seal and cause inadvertent mixing of the fluid in the inner barrel with the material in the outer barrel. It is a further object of the invention to provide such a seal which will improve the mixing between the fluid contained in the inner barrel and the material contained in the outer barrel. Other objects will be apparent from the following disclosure and claims.

BRIEF DESCRIPTION OF THE INVENTION

The invention is based on three primary discoveries and several subsidiary discoveries. The first discovery is that in order to make the seals inexpensively, the seals must not require exceptionally accurate molding, such as is required in producing a biased seal in the nature of the above-discussed U.S. Pat. No. 3,685,514. To this end, the present invention provides a seal where accurate molding is not required, since the arrangement of the seal is such that it will accommodate reasonable manufacturing tolerances in producing the seal. This is a result of the seal having a cylindrical portion of resilient and compressible material with a diameter such that it is compressibly disposed in the aperture. Thus, normal manufacturing tolerances can easily be accommodated by the seal in that it is placed into the aperture under compression and some undersizing or oversizing will not materially affect the fluid tightness of the seal.

In a sense, therefore, the present arrangement is self-compensating for manufacturing tolerances.

A second discovery is that in order for a seal to be inexpensive, it must be capable of manufacture by relatively simple molding techniques and not require intricate and difficult to operate molds. This is achieved in the present invention by the seal consisting of a single plug which can be monolithically molded and, for the reasons noted above, does not require accurate and demanding molding techniques, since considerable molding tolerances can be easily accommodated.

A third discovery is that when the seal is compressibly, but resiliently held in the aperture, it will remain in that position until a critical pressure is generated in the fluid in the inner barrel. Once the critical pressure is exceeded, the seal quickly moves out of the aperture and allows the fluid in the inner barrel to quickly exit the aperture. This is achieved in the present invention by a reduced diameter portion of the plug which provides a fluid pathway between the aperture and the plug when the cylindrical portion is displaced from the aperture. In a sense this can be analogized as a nozzle-like arrangement for increasing the linear speed of the fluid passing through the aperture. This, of course, significantly increases the mixing efficiency in that it causes the fluid to be dispersed in the outer barrel which substantially improves mixing of the fluid and the material in the outer barrel.

As a further subsidiary discovery, if the plug is abruptly halted, after the cylindrical portion is forced from the aperture, this will cause the fluid passing through the aperture to impinge upon the plug and cause further dispersion of the fluid for mixing purposes. This is achieved in the present invention by providing an increased diameter portion of the plug which prevents the plug from passing through the aperture into the outer barrel and abruptly halts the plug once the cylindrical portion has passed out of the aperture. With such impingement, a shower-like dispersion of the fluid can be achieved and this further enhances the mixing ability.

As another subsidiary discovery, in the above regard, at the lowermost end of the cylindrical portion, a raised portion, generally in the form of a flange, may be provided. This raised portion not only prevents the plug from passing through the aperture into the inner barrel during assembly, but forms an additional seal to insure a leak proof arrangement and, even more importantly, provides an additional impingement of the fluid for increasing the dispersing of the fluid and even better mixing.

Thus, briefly stated, the present invention is in a seal for a two compartment mixing syringe having an outer barrel with cannula end and opposite open end and an inner barrel which is partially disposed within the outer barrel and has an open end and an opposite dispensing end with a displaceable seal thereon. A plunger is partially disposed within the inner barrel, such that when pressure is applied by digital movement of the plunger into the inner barrel to a fluid contained within a first compartment defined by the plunger and the inner barrel, the displaceable seal is displaced and the fluid in the first compartment flows into and is mixed with a material in a second compartment defined by the outer barrel and the inner barrel. By digital movement of the inner barrel within the outer barrel the resulting mixture is passed through the cannula and out of the syringe.

The present improvement is in the foregoing seal for the two compartment mixing syringe and comprises a seal having in combination an aperture in the dispensing end of the inner barrel and plug disposed in the aperture. The plug comprises a cylindrical portion of resilient and compressible material with a diameter such that it is compressibly disposed in the aperture and seals the aperture against fluid leakage therethrough, but is displaceable from the aperture by fluid pressure exerted by digital movement of the plunger into the inner barrel. A reduced diameter portion is provided such that when the cylindrical portion is displaced from the aperture a fluid pathway from the inner barrel to the outer barrel is provided between the aperture and the reduced diameter portion. An increased diameter portion is provided such that when the cylindrical portion is displaced from the aperture and the fluid pathway is provided, the increased diameter portion prevents the plug from passing through the aperture and into the outer barrel.

BRIEF DESCRIPTION OF THE DRAWINGS

FIG. 1 is a cross-sectioned side view of the syringe of the present invention showing the present seal;

FIG. 2 is a cross-sectioned side and enlarged view of the seal of the present invention, and showing a portion of the end walls of the dispensing end of the inner barrel surrounding the aperture of the seal;

FIG. 3 is a top view of the plug of the present invention;

FIG. 4 is top view of the seal of the present invention and showing a portion of the end walls of the dispensing end of the inner barrel surrounding the seal of the present invention; and FIG. 5 is a partially cross-sectional view showing variation of the seal of the present invention.

DETAILED DESCRIPTION OF THE INVENTION

Referring first to the FIG. 1, which shows a typical cross-sectioned side view of a two compartment mixing syringe, the syringe, generally, 1 has an outer barrel 2 with a cannula end 3 having a cannula 4 and an opposite open end 5.

An inner barrel 8 is partially disposed with an outer barrel 2 and has an open end 9 and an opposite dispensing end 10 with a displaceable seal, generally, 11, thereon. A plunger 15 is partially disposed with an inner barrel 8. The plunger has a digit receiving means 16, e.g. a flat plate or the like, and a plunger seal 17. Typically, the plunger will have ribs 18 for providing a rigid support for the plunger. Outer barrel 2 has finger grips 19 and similarly inner barrel 8 has finger grips 20.

The syringe will normally be provided with a cannula cap 21 for snugly fitting over cannula 4. In addition, or alternatively, a needle (not shown) may be fitted on cannula 4.

The syringe is composed of two compartments. A first compartment 25 is defined by the plunger 15 (more specifically by the lowermost end 26 of a plunger seal 17) and the inner barrel 8. A second compartment 27 is defined by outer barrel 2 and inner barrel 8 (more specifically the lowermost end 28 of inner barrel 8).

As can thus be seen from FIG. 1, digital movement of plunger 15 into inner barrel 8 will apply pressure to a fluid contained within first compartment 25. That fluid pressure will eventually cause displacement of seal 11 and the fluid in the first compartment will flow into and mix with a material in second compartment 27. By continued movement of plunger 15 into inner barrel 8, eventually, plunger 15 will be fully disposed in inner barrel 8 and all of the fluid contained in the first compartment 25 will have flowed into the second compartment 27.

After mixing of the fluid flowed from first compartment 25 with the material contained in second compartment 27, that mixture is expelled from the syringe by digital movement of inner barrel 8 into outer barrel 2. With continued movement of inner barrel 8 into outer barrel 2 all of the mixture is passed through cannula 4 and out of the syringe.

For sake of conciseness, the operation and construction of two compartment syringes will not be described beyond that provided above, since these two compartment syringes are well known to the art. This is particularly true since the present invention centers around seal 11 used in such two compartment syringes.

In this latter regard, the present improvement comprises a seal 11 having in combination an aperture 30 in the dispensing end 10 of inner barrel 8 and a plug 31 disposed in the aperture.

Referring now more specifically to FIGS. 2 through 4, but with general reference to FIG. 1, the plug 31 comprises a cylindrical portion 32 which is made of a resilient and compressible material (described more fully hereinafter). The diameter of cylindrical portion 32 is such that the cylindrical portion is compressibly disposed in aperture 30 which seals the aperture against fluid leakage therethrough. However, this compressible disposition of cylindrical portion 32 in aperture 30 also allows cylindrical portion 32 to be displaced from the aperture by fluid pressure exerted by the digital movement of plunger 15 into inner barrel 8.

Plug 31 also has a reduced diameter portion 35. This reduced diameter portion 35 is so configured that when the cylindrical portion 32 is displaced from aperture 30 a fluid pathway is provided between aperture 30 and the reduced diameter portion 35.

Plug 31 also has an increased diameter portion 38 such that when the cylindrical portion 32 is displaced from aperture 30 and the fluid pathway is provided between reduced diameter portion 35 and aperture 30, the increased diameter portion 38 prevents the plug 31 from passing through aperture 30 and into outer barrel 2.

Preferably, the cylindrical portion 32 has a raised portion 39 at its lowermost end such that the raised portion substantially prevents plug 31 from passing through aperture 30 and into inner barrel 8. Most preferably the raised portion 39 is in the form of a truncated ring, as shown in FIG. 2, such that the truncated ring seats against the walls 40 and effects further sealing of the plug 31 in aperture 30. The truncated form also provides centering of plug 31 in aperture 30 when the plug is assembled from within inner barrel 8 by a conventional mechanical/vacuum jig. Alternately the plug 31 may be assembled into aperture 30 when the increased diameter portion 38 is a partially cut-out ring portion, as shown in FIG. 3, such that the plug may be inserted into aperture 30 by folding the partially cut-out ring portions and pressing them through aperture 30 and into inner barrel 8, as shown in FIG. 1.

By virtue of cylindrical portion 32 being made of resilient and compressible material and having a diameter such that it is compressibly disposed in aperture 30, it is also possible to configure cylindrical portion 32 with a diameter such that the plug is not displaceable from aperture 30 until a substantial pressure is exerted on a fluid contained in the first compartment 25. As will be appreciated, when cylindrical portion 32 is compressibly disposed in aperture 30, it will not be displaced from aperture 30 until the fluid pressure in first compartment 25 reaches a value sufficient to overcome that resilient compression of cylindrical portion 32. By choosing an appropriate diameter for cylindrical portion 32, that pressure required to displaced cylindrical portion 32 from aperture 30 can be varied widely and can be a substantial fluid pressure which will avoid inadvertent mixing of the fluid with the material in second compartment 27. It will also be appreciated that when that pressure, including substantial pressure, is exceeded the cylindrical portion 32 being resilient, will most quickly exit aperture 30, and that plug 31 will come to an abrupt halt when increased diameter portion 38 contacts the inside surface 43 of inner barrel 8 dispensing end 10. This causes fluid passing from the first compartment 25 into the second compartment 27 to impinge against cylindrical portion 32 and produce a dispersed form of the fluid which, thus, improves the mixing of the fluid with the material in second compartment 27.

Referring more specifically to FIG. 4, the cut-out portion, generally 45, of the increased diameter portion 38 (shown as a cut-out ring in FIGS. 2 through 4) is such that the cut-out portions 45 have a diameter less than the diameter of aperture 30 (as more clearly seen in FIG. 4). Indeed the diameter of the cut-out portions may be the same as the diameter of the reduced diameter portion 35, as shown in FIG. 3. Thus, as will be appreciated, a fluid pathway is provided through aperture 30 when plug 31 is displaced from aperture 30.

For convenience of manufacture and as can be appreciated from the above, all of the components of plug 31 may be made of the same material, e.g. all of the cylindrical portion 32, reduced diameter portion 35, and increased diameter portion 38 are made of a resilient and compressible material, as may be raised portion 39. This allows the entire plug to be molded as a single monolithic unit in a single molding operation. It should be appreciated, however, if desired, such a single monolithic molding need not be used and it is only necessary that cylindrical portion 32 be made of the resilient and compressible material. The other portions of plug 31 may be made of rigid and even non-moldable materials, e.g. metal, if desired, although this is certainly not the preferred embodiment of the invention.

Preferably, the resilient and compressible material is a polymeric material, e.g. a rubber or plastic, and more preferably rubber. Any of the usual moldable rubbers may be used in this regard, or any of the soft, compressible and resilient plastics. Indeed, a non-compressible and non-resilient plastic may be used when it is in a foamed form which will provide a resilient and compressible material, e.g. foamed polyethylene, polypropylene, polyvinylchloride, polyurethane and the like.

Turning now to FIG. 5, that figure shows a modification of the present seal. The modification is that aperture 30 is disposed within a recess 48. Otherwise the arrangement is the same as described above. The purpose of recess 48 is that when cylindrical portion 32 is displaced from aperture 30, it will essentially remain in recess 38 and the lowermost end 28 of inner barrel 8 can essentially fully seat and contact lowermost inside surface 50 of outer barrel 2 (see FIG. 1). This will cause essentially all of the mixture in second compartment 27 to be expelled through cannula 4. It will be appreciated that in a typical application, second compartment 27 will have the active ingredients, e.g. a pharmaceutical powder, while first compartment 25 will have a diluent or solvent therefor. If some small amount of diluent or solvent is left in first compartment 25, this is of no substantial concern, but leaving a substantial amount of the mixture in second compartment 27 could affect the accuracy of dosing.

The size of aperture 30 and plug 31 is not narrowly critical, but it will be appreciated that the sizes thereof will affect the pressure required on the fluid in first compartment 25 to displace plug 31 from aperture 30. Thus, the larger the diameter of cylindrical portion 32, the less absolute pressure required in first compartment 25 to displace the plug 31. Generally, the diameter of cylindrical portion 32 should be at least ⅛th the diameter of inner barrel 8 and up to ¾ths of the diameter of inner barrel 8. More usually, however, the diameter of cylindrical portion 32 will be between about ¼th and ⅔rds of the diameter of inner barrel 8. It will also be appreciated that reduced diameter portion 35 should have a length such that cylindrical portion 32 can fully pass through aperture 30 before increased diameter portion 38 contacts inside surface 43 of dispensing end 10. Thus, that length of reduced diameter portion 38 will be at least slightly more than the thickness of dispensing end 10.

The size of the aperture is not critical and is chosen in combination with the diameter of cylindrical portion 32. Generally, however, the diameter of aperture 30 is from 95% to 65% of the diameter of cylindrical portion 32, and more usually from 92% to 80%, e.g. 90% to 85%.

In the foregoing description of the invention, the term "diameter" has been used for sake of simplicity. However, it will be easily appreciated that it is not necessary for the "diameters" referenced to be that of a circular cross-section. Indeed, all of the diameters referenced may be in other cross-sectional shapes, e.g. elliptical, rectangular, square, triangular or the like. Therefore, in connection with the present disclosure and following claims, the term "diameter" is defined to mean the cross-sectional distance of the element defined. However, normally, all of the "diameters" will be configured with circular cross-sections.

The present invention is useful with a variety of combinations of materials disposed in first compartment 25 and second compartment 27. However, it will be appreciated that the material in first compartment 25 must be a fluid, e.g. a liquid, since a solid will not adequately distribute pressure generated thereon by plunger 15. However, the material in second compartment 27 may be either a fluid, e.g. a liquid, or a solid, e.g. a powder. Typical examples are where first compartment 25 contains a solvent or diluent and second compartment 27 contains a powdered pharmaceutical dissolvable therein or where first compartment 25 contains a liquid activator and second compartment 27 contains a adhesive or sealant. Another example is where first compartment 25 contains a chemical blowing agent, while second compartment 27 contains a foamable plastic for providing a foamed plastic for sealing, laminating and the like.

Turning now to the manufacture and details of operation of the syringe of the present invention, the syringe may be a disposable syringe or it may be a reusable syringe. Thus, when the syringe is molded of an inexpensive plastic, e.g. polyethylene, polypropylene, polyvinylchloride or the like, the syringe may be so inexpensively manufactured that it is disposable. On the other hand, the syringe may be made of metal, glass or the like where reuse is intended. Plug 31, as noted above, is preferably a rubber material. In any event, since the plug is made of a resilient and compressible material, it may be easily inserted, during manufacture of the syringe, into aperture 30 by either folding raised diameter portion 38 (see specifically FIG. 3) and inserting those raised portions through aperture 30 and into inner barrel 8 or by pressing truncated raised portion 39 from inside barrel 8 through aperture 30 with an appropriate jig. This allows a very simple and inexpensive assembly of the present syringe and seal. Further, when plug 31 is made of a rubber or the like, it can be inexpensively molded as a monolithic unit in a single injection molding operation. This makes the plug exceedingly inexpensive to manufacture, and since it can be very easily inserted into the aperture, assembly is also very inexpensive.

As noted above, by choosing the correct diameter of cylindrical portion 32, substantial pressures can be required before plug 31 is displaced from the aperture. This provides an excellent safety feature for the present syringe, since that plug cannot be inadvertently displaced during handling of the syringe where plugger 15 may be moved into inner barrel 8. This is opposed to the bias seal of U.S. Pat. No. 3,685,514, where relatively small amounts of pressure can overcome that bias and the seal may leak fluid into the compartment 27.

An important feature of the present invention is the ability to cause the fluid to be dispersed when passing through aperture 30, as described above. This is particularly important where the material in second compartment 27 is a powder subject to lumping on initial wetting. When the fluid is relatively slowly passed into second compartment 27 such lumping can occur and this can make dissolution difficult. On the other hand, where the present impingement and dispersing of the fluid into droplets or shower form, occurs, this will quickly and evenly wet a powdered material and avoid lumping, with the attendant avoidance of difficult dissolution.

In operation, according to the foregoing, when pressure is applied to plunger 15, the plunger will move into barrel 8, but until the pressure is increased to the value necessary to overcome the resilient disposition of plug 31 in aperture 30, plug 31 will not be displaced from aperture 30. However, when that pressure exceeds that necessary to displace plug 31, that plug is quickly displaced and the pressure applied to plunger 15 in displacing the plug will cause a very quick exit of the fluid from first compartment 25. This is opposed to the relatively slow movement of prior art two compartment syringes and the attendant propensity of those prior syringes to cause lumping of powdered material in second compartment 27.

Also, in order to avoid an inadvertent displacement of barrel 8 into barrel 2, barrel 2 may have a ridge 52 (see FIG. 1) on the inside surface thereof. This will help prevent movement of barrel 8, inadvertently, into barrel 2. Of course, the ridge should be such that when it is desired to move barrel 8 into barrel 2, the resistance of the ridge can be overcome.

Thus, it will be seen that the objects of the invention have been achieved. However, it will be appreciated by those skilled in the art that obvious modification of the above-described embodiments are apparent and it is intended that those modifications be embraced by the spirit and scope of the annexed claims.

It is claimed:

1. In a seal for a two compartment mixing syringe having an outer barrel with a cannula end and an opposite open end, and inner barrel partially disposed within the outer barrel and having an open end and an opposite dispensing end with a displaceable seal thereon, and a plunger partially disposed within the inner barrel, such that when pressure is applied by digital movement of the plunger into the inner barrel to a fluid contained within a first compartment defined by the plunger and the inner barrel, the displaceable seal is displaced and the fluid in the first compartment flows into and is mixed with a material in a second compartment defined by the outer barrel and the inner barrel, and by digital movement of the inner barrel within the outer barrel the resulting mixture is passed through the cannula and out of the syringe, the improvement comprising a said seal having in combination an aperture in the dispensing end of the inner barrel and a monolithic plug made of a single resilient and compressible material and disposed in the said aperture, said plug comprising:

a cylindrical portion of said resilient and compressible material with a diameter such that it is compressibly disposed in said aperture and seals said aperture against fluid leakage therethrough but is displaceable from said aperture by fluid pressure exerted by digital movement of the plunger into the inner barrel;

a reduced diameter portion such that when said cylindrical portion is displaced from said aperture a fluid pathway from the inner barrel to the outer barrel is provided between the aperture and the reduced diameter portion; and an increase diameter portion with a diameter greater than the diameter of the cylindrical portion such that when the cylindrical portion is displaced from said aperture and the said fluid pathway is provided, the increased diameter portion prevents the said plug from passing through said aperture and into the outer barrel; and wherein the cylindrical portion is of such a diameter that the plug is not displaceable from the aperture until substantial fluid pressure is exerted into the first compartment and when that said substantial pressure is exceeded, the cylindrical portion quickly exits the aperture and comes to an abrupt halt when the increased diameter portion contacts the inside surface of the inner barrel dispensing end, and whereby the fluid passing from the first compartment impinges against the cylindrical portion and produces a dispersed form of the fluid which, thus, improves the mixing of the fluid with the material in the second compartment.

2. The seal of claim 1 wherein the cylindrical portion has a raised portion at its lowermost end such that the raised portion substantially prevents the plug from passing through the aperture and into the inner barrel.

3. The seal of claim 2 wherein the raised portion is in the form of a ring at the lowermost end of the cylindrical portion such that when the seal is in place the ring seats against the walls of the dispensing end of the inner barrel surrounding the aperture and effects further sealing of the plug in the aperture.

4. The seal of claim 1 wherein the increased diameter portion is in the form of partially cut-out ring portion such that the plug may be inserted into the aperture by folding the partially cut-out ring portions and pressing it through the aperture and into the inner barrel.

5. The seal of claim 3 wherein said impingement also is against the raised portion at the lowermost end of the cylindrical portion.

6. The seal of claim 4 wherein the cut-out portion of the said ring portion is such that the cut-out portions have a diameter less than the diameter of the aperture whereby a fluid pathway is provided when the plug is displaced from the aperture.

7. The seal of claim 1 wherein the resilient and compressible material is a polymeric material.

8. The seal of claim 7 wherein the polymeric material is a rubber or plastic.

9. The seal of claim 7 wherein the polymeric material is a rubber.

10. The seal of claim 1 wherein the plug is a single molded unit.

11. The seal of claim 1 wherein the aperture is disposed within a recess, and when the cylindrical portion is displaced from the aperture it will essentially remain in that recess.

12. The seal of claim 1 wherein the diameter of the aperture is from 95% to 65% of the diameter of the cylindrical portion.

* * * * *